US006995009B1

(12) United States Patent
Kitamura et al.

(10) Patent No.: US 6,995,009 B1
(45) Date of Patent: Feb. 7, 2006

(54) PACKAGING CELL

(75) Inventors: Toshio Kitamura, Tokyo (JP); Sumiyo Morita, Tokyo (JP)

(73) Assignees: Chugai Seiyaku Kabushiki Kaisha, Tokyo (JP); Toshio Kitamura, Tokyo (JP)

( * ) Notice: Subject to any disclaimer, the term of this patent is extended or adjusted under 35 U.S.C. 154(b) by 149 days.

(21) Appl. No.: 10/009,329

(22) PCT Filed: Jun. 1, 2000

(86) PCT No.: PCT/JP00/03557

§ 371 (c)(1),
(2), (4) Date: Apr. 11, 2002

(87) PCT Pub. No.: WO00/73423

PCT Pub. Date: Dec. 7, 2000

(30) Foreign Application Priority Data

Jun. 1, 1999 (JP) .................................. 11-154364
Jan. 21, 2000 (JP) ............................... 2000-17831

(51) Int. Cl.
*C12N 15/00* (2006.01)

(52) U.S. Cl. ................ 435/320.1; 435/325; 435/235.1; 435/456; 435/69.1

(58) Field of Classification Search ................ 435/325, 435/235.1, 320.1, 456, 69.1
See application file for complete search history.

(56) References Cited

U.S. PATENT DOCUMENTS

2002/0123146 A1 * 9/2002 Klatzmann et al. ......... 435/456

FOREIGN PATENT DOCUMENTS

| WO | WO 98/02529 | 1/1998 |
| WO | WO 99/64568 | 12/1999 |

OTHER PUBLICATIONS

Hobbs et al., Biochem Biophys Res Comm 199 vol. 252, pp. 368-372.*

Duisit et al., "Functional Characterization of Adenoviral/Retroviral Chimeric Vectors and Their Use for Efficient Screening of Retroviral Producer Cell Lines," *Human Gene Therapy*, 10:189-200 (Jan. 20, 1999).

Kitamura et al., *Jikken Igaku Bessatsu, Shin Idenshi kouguku Handbook,* pp. 245-9 (1998).

Kitamura et al., "New experimental approaches in retrovirus-mediated expression screening", *International Journal of Hematology,* 67 (1998), pp. 351-359.

Morita et al., "Plat-E: an efficient and stable system for transient packaging of retroviruses", *Gene Therapy,* (2000) 7:1063-1066.

Pear et al., "Production of high-titer helper-free retroviruses by transient transfection", *Proc. Natl. Acad. Sci. USA,* vol. 90, pp. 8392-8396.

Yogalingam et al., "Regulation of N-Acetylgalactosamine 4-Sulfatase Expression in Retrovirus-Transduced Feline Mucopolysaccharidosis Type VI Muscle Cells", *DNA and Cell Biology,* vol. 18, No. 3 (1999), pp. 187-195.

A tutorial of Phoenix Ecotropic and Amphotropic Packaing Lines.

A tutorial of Improvements to retroviral producer lines; Phoenix Systems.

Hobbs et al., "Development of a bicistronic vector driven by the human polypeptide chain elongation factor Ialpha promoter for creation of stable mammalian cell lines that express very high levels of recombinant proteins," *Biochemical and Biophysical Research Communications,* vol. 252, No. 2, Nov. 18, 1998, pp. 368-372.

Rigg et al., "A Novel Human Amphotropic Packaging Cell Line: High Tilter, Complement Resistance, and Improved Safety" *Virology,* vol. 218, No. 1, 1996, pp. 290-295.

Swift et al., "Rapid production of retroviruses for efficient gene delivery to mammalian cells using 293T cell-based systems," *Current Protocols in Immunology,* Supp. 31, 1999, pp. 10.17.14-10.17.29.

Yang et al., "Generation of Retroviral Vector for Clinical Studies Using Transient Transfection," *Human Gene Therapy,* vol. 10, No. 1, Jan. 1, 1999, pp. 123-132.

* cited by examiner

*Primary Examiner*—James Housel
*Assistant Examiner*—Myron G. Hill
(74) *Attorney, Agent, or Firm*—Fish & Richardson P.C.

(57) ABSTRACT

A virus-producing cell sustaining the ability to produce viruses at high titer is successfully constructed by expressing the virus structural gene under the regulation of EF1α promoter. In this virus-producing cell, the virus structural gene is ligated to a selection marker gene via IRES and domains other than the protein coding domain are eliminated from the DNA encoding virus structural proteins. Thus, reduction of the titer due to cell passages can be prevented and emergence of wild type viruses caused by unfavorable recombination of the virus genome can be inhibited.

17 Claims, No Drawings

PACKAGING CELL

This application is a National Stage Entry of PCT/JP00/03557, filed Jun. 1, 2000, which claims priority to Japan 11/154,364, filed Jun. 1, 1999, and Japan 2000-17831, filed Jan. 21, 2000.

TECHNICAL FIELD

The present invention relates to a virus-producing cell (packaging cell) that stably retains the ability to produce high titer viruses and the use of such a cell for virus production.

BACKGROUND ART

Retroviral vectors are capable of transferring genes with high efficiency and stability to host cells. Thus, they are used in gene transfer methods, for transferring genes into cells in a variety of fields including the field of medicine. Generation of retroviral vectors has been developed based on the genetic structure and the life cycle mechanism of retroviruses. The fundamental principle is to transfer the gene of interest into a retroviral vector possessing a packaging signal but lacking each of the gag, pol, and env structural genes, then introducing the retroviral vector into a packaging cell possessing each of the gag, pol, and env structural genes lacking a packaging signal. Then, a virus particle containing the retroviral vector RNA is formed (i.e. packaged), and finally, retroviruses are produced into the supernatant of a cell culture (Kitamura, T., International Journal of Hematology, 67:351–359 (1998)). Retroviruses produced in this manner can efficiently transfer the genes of interest into cells. Simultaneously, since they lack each of the gag, pol, and env structural genes, they can replicate only within the packaging cells and cannot replicate within normal cells. Therefore, functional retroviruses are unlikely to regenerate from the prepared infected cells.

The production of packaging cells with such characteristics is disclosed in international publication numbers WO90/02806, WO94/19478, WO96/34098, and so on. However, the prior art is unsatisfying in terms of infection efficiency and long-term stability. In addition, to increase the titer of the viruses, it is necessary to express the viral structural proteins in a large amount within the packaging cell. Packaging cells that can express a large amount of viral structural proteins and show a limited reduction in titer of viruses produced through passages are needed in the art.

DISCLOSURE OF THE INVENTION

The object of this invention is to provide a virus-producing cell having the ability to produce infectious viruses at high titers. In a preferred embodiment of the present invention, virus-producing cells with enhanced long-term stability and safety are provided. Another object of this invention is to provide a method for producing infectious viruses at high titers using the virus-producing cells.

To accomplish the objects described above, the present inventors first searched for a promoter having a high activity in 293T cells. Upon investigating the strength of transcription activity of the SV40 promoter, SRα promoter, EF1α promoter, TK promoter, MuLV LTR, and CMV LTR, the present inventors found that the activities driven by the EF1α promoter and the CMV promoter were remarkably high compared to those of the other promoters. Accordingly, an attempt was made to establish high-performance packaging cells using the EF1α promoter.

Specifically, the present inventors used only coding sequence for the gag-pol and env genes in the packaging constructs under the regulation of the EF1α promoter in order to enhance the expression efficiency of the genes encoding the viral structural proteins in the packaging cells. Furthermore, to enhance the translation efficiency of the viral structural proteins from the transcribed mRNAs, Kozak's consensus sequence (GCCACC) was inserted upstream of the translation initiation codon of these genes. In addition, a selective marker resistant gene was linked via the IRES sequence (internal ribosomal entry site) downstream of these genes, so that the genes positioned upstream and downstream of the IRES are translated from a single mRNA. This enabled reliable selection of cells expressing the inserted construct by the selective marker. In this manner, cells were produced having superior long-term stability compared to conventional packaging cells by separately introducing a construct containing the selective marker resistant gene and, a construct containing the gag-pol and env genes.

In addition, improvement in safety was achieved by inserting the gag-pol and env genes produced by PCR amplification of only the viral structural proteins encoding regions into the construct, thus eliminating the possibility of emergence of wild type viruses from the packaging cells due to recombination.

The present inventors examined the performance of the packaging cells produced in this manner and found out that the packaging cells produced high-titer retroviruses. Even after a long-term passage of 4 months, they retained the ability to produce retroviruses at the same level of titer as before. The packaging cells of this invention are useful for producing vectors for gene transfer to a living body, and may be preferably utilized especially for producing high-titer retroviral vectors used for gene therapy, and such.

That is, the present invention relates to methods for producing a virus-producing cell having superior safety, retaining the ability to produce infectious viruses at high titer even after long-term passages, and to methods for producing infectious viruses at high titer using the virus producing cells. More specifically, this invention provides the following:

(1) a cell for the production of retroviruses, wherein the cell has an expression construct comprising a DNA encoding retroviral structural proteins operably linked downstream of an EF1α promoter;

(2) the cell according to (1), wherein the DNA encoding retroviral structural proteins is a DNA encoding any one or more of the proteins selected from the group consisting of gag, pol, and env;

(3) the cell according to (2) that expresses all of gag, pol, and env;

(4) the cell according to (3), which has an expression construct expressing gag and pol, and an expression construct expressing env;

(5) the cell according to (3) or (4), wherein the env is derived from either an ecotropic retrovirus or amphotropic retrovirus;

(6) the cell according to any one of (1) to (5), wherein a Kozak's consensus sequence is placed upstream of the translation initiation codon of the DNA encoding the retroviral structural proteins in the expression construct;

(7) the cell according to any one of (1) to (6), wherein the DNA encoding the retroviral structural proteins is bound via the IRES sequence to a DNA encoding a selective marker;

(8) the cell according to any one of (1) to (7), wherein the DNA encoding the retroviral structural proteins is substantially free of virus genome-derived DNA with the exception of the protein coding region;

(9) the cell according to any one of (1) to (8), wherein the cell is derived from 293 cells;

(10) the cell according to (9), wherein the cell is derived from 293T cells;

(11) the cell specified by the accession No. FERM BP-6737 or FERM BP-6977;

(12) a method for producing a retrovirus, comprising the steps of: introducing a retroviral vector DNA lacking at least one of the genes encoding a viral structural protein into the cell of any one of (1) to (11);

(13) the method according to (12), wherein the retroviral vector DNA lacks all of the genes encoding the gag, pol, and env;

(14) the method according to (12) or (13), wherein a foreign gene is included in the retroviral vector DNA; and

(15) a retrovirus produced by the method of any one of (12) to (14).

The packaging cells of this invention are characterized by their use of the EF1α promoter for the expression of retroviral structural proteins. The present inventors searched for a promoter that has a high activity in packaging cells. As a result, it was found out that the EF1α promoter had an especially strong activity among the promoters whose activity could be detected. The packaging cells of this invention highly-express the retroviral structural protein due to the use of the EF1α promoter, which, in turn, enables the production of high-titer virus particles.

A DNA encoding the retroviral structural protein(s) is expressed under the regulation of the EF1α promoter in a packaging cell by producing an expression construct in which the DNA encoding the retroviral structural protein(s) is operably linked downstream of the EF1α promoter, and then, introducing it into the cell. The term "operably linked" used herein indicates that the EF1α promoter is bound to the DNA such that its activation ensures the expression of the downstream DNA encoding the retroviral structural protein.

Examples of the retroviral structural proteins expressed in the cells are the gag, pol, and env. Theoretically, it is not necessary to express all of these proteins in the packaging cells and it is possible to place genes encoding some of these proteins on the retroviral vector DNA. For example, it is possible to have the packaging cells express the gag and pol, whereas the env gene is placed on the retroviral vector DNA. However, in this case, there is the possibility that the amount of env expression would not reach the required amount. Therefore, it is preferable that all of gag, pol, and env are expressed by the packaging cells themselves.

The expression construct is preferably separated into a construct expressing the gag and pol, and a construct expressing the env, which are then introduced into the cell. In this manner, the possibility that self-replicating viruses will be produced, due to the recombination of pol, gag, and env that often occurs among those existing on the retroviral vector and those in the packaging cell, will be reduced. This is important from the view of safety, for example, when using the viruses produced by these cells in gene therapy. Regarding gag and pol, it is preferable to have them encoded as gag-pol on a same construct. This is because it is known that the expression ratio between pol and gag is important for the production of high-titer viruses and expression of pol alone at large quantities, which may occur by making separate expression constructs of gag and pol, will cause toxicity towards the cell.

It is possible to prepare packaging cells using env, if desired, derived from ecotropic retroviruses (referred to as ecoenv) or amphotropic retroviruses (referred to as amphoenv). Packaging cells having ecoenv produce ecotropic retroviruses whereas packaging cells having amphoenv produce amphotropic retroviruses. Since the ecotropic retrovirus has a glycoprotein binding to the ecotropic receptor that exists only on the cell surface of rat and mouse, they only infect rat and mouse cells. On the other hand, the amphotropic retrovirus is capable of infecting various species, such as rat, mouse, humans, chicken, dog, cat, etc. An example of a retrovirus used in gene therapy is the amphoenv, which is capable of infecting humans. However, to clone novel genes in the laboratory, it is safer to use retroviruses produced from packaging cells that carry ecoenv with no infectivity to human.

Various retroviral env, such as env derived from Rous sarcoma virus (RSV), may be used (Landau, N. R. and Littman, D. R., (1992) J. Virology 5110–5113)). Furthermore, envelope proteins other than those from retroviruses may be used. For example, it is possible to use vesicular stomatitis virus (VSV)-derived G protein (VSV-G) (Ory, D. S. et al., (1996) Proc. Natl. Acad. Sci. USA 93: 11400–11406).

In a preferred embodiment of this invention, the Kozak's consensus sequence (GCCACC) is placed upstream of the translation initiation codon (ATG) of the retroviral structural protein gene within the expression construct to increase the translation efficiency of mRNA encoding these proteins transcribed from the expression constructs for expression of retroviral structural proteins (the Kozak's rule reveals that it is highly probable that a GCCACC sequence exists in front of the translation initiation site ATG).

In another preferred embodiment, this invention provides packaging cells harboring expression constructs that express the viral structural protein(s) and a selective marker simultaneously by operably linking the DNA encoding the viral structural protein(s) and selective marker via the IRES. The viral structural protein(s) and selective marker are encoded on a single molecule transcribed by EF1α activation in the expression construct. Thus, not only the protein (s) but also the selective marker is translated by the action of IRES from the RNA molecule. Accordingly, reliable selection of cells expressing the retroviral structural protein(s) by the selective marker becomes possible due to the transformation with the expression construct. Conventionally, packaging cells were produced by separately introducing an expression construct carrying the selective marker resistant gene and an expression construct carrying the gag-pol and env genes into cells. Thus, the cells harboring the selective marker resistant gene and those harboring the viral structural protein genes were not always consistent, which caused problems in terms of the stability of the cells. The utilization of the IRES sequence enables the preparation of packaging cells with excellent long-term stability.

In addition to blasticidin and puromycin described in the examples, for example, hygromycin, diphtheria toxin, neomycin, and such may be used as selective markers. However, blasticidin and puromycin are preferable since they act quickly and require shorter time for selection of cells as compared to other drugs. The resistant genes of diphtheria toxin and hygromycin are described in "Bishai, W. R. et al., J. Bacteriol., 169: 1554–1563 (1987)" and "hygromycin: Yin, D. X. et al., Cancer Res., 55: 4922–4928 (1995)", respectively.

In a further preferred embodiment, this invention provides cells harboring an expression construct in which the DNA encoding retroviral structural protein(s) under the regulation of EF1α is substantially free of DNA other than that of the protein coding region. In the packaging cells of this invention, it is preferable to maximally remove viral genome-derived sequences that are not essential for expression of structural proteins. This allows one to cut down to a minimum the risk of emergence of replication-capable retroviruses (RCR) by reducing the possibility of recombination between the viral genome-derived DNA and retroviral DNA within the expression construct after the retroviral vector DNA is transferred into packaging cells that have above-mentioned expression constructs. This, in turn, enables improvement of the safety of the virus particles produced from the packaging cells.

DNA that is substantially free of DNA, other than that of such retroviral structural protein coding regions, may be obtained, for example, by a polymerase chain reaction using the viral genome DNA as the template and primers corresponding to the viral structural protein coding regions as described in the following examples. Herein, "is substantially free of" DNA other than that of the coding region means that DNA other than that of the viral genome-derived protein coding region is 30 or less, preferably 10 or less, more preferably 5 or less, and most preferably 0 bases.

For example, NIH3T3 (mouse fibroblast), 293 (human fetal kidney cells) (Graham, F. L., J. Gen. Virol., 36, 59–72 (1977)), and such may be used as host cells for the production of packaging cells. However, the invention is not limited thereto, so long as the cells have a high transfection efficiency.

The calcium phosphate method, electroporation method, and general transfection methods with lipofectamine (GIBCO BRL), Fugene (Boehringer Mannheim), and such may be used to introduce expression constructs into the cell. Drug selection may be used as the selection method. For example, blasticidin, puromycin, hygromycin, diphtheria toxin, neomycin, and such may be used as the drug for drug selection, without limitation so long as the drug tolerance gene is known.

Preferably, the retroviral vector DNA is introduced into each clone of the obtained packaging cells following limiting dilution of the cells. Then, through measurement of the titer of the produced viruses, cells producing viruses with the highest titer are selected and cloned.

There is no particular limitation on the retroviral vector DNA inserted into the packaging cells. When the packaging cells are derived from cells expressing the SV40 large T antigen, as in the 293T cells, the use of vector DNA bound to the replication initiation site of SV40 enables an increase in the number of its copies produced within the packaging cells, and thus an increase in titer can be expected.

Introduction of retroviral vector DNA into cells can be carried out by the same method as that described above for the introduction of the viral structural protein expression constructs into cells. The retroviral vector of interest can be prepared by harvesting the retroviral particles released into the supernatant of the packaging cell culture after the introduction of the retroviral vector.

The retroviral vectors produced by the packaging cells of this invention may be utilized in comprehensive fields of research and medicine. For example, they may be used as vectors for expressing the gene of interest ex vivo or in vivo in gene therapy and in the production of animal models. They may be also useful as vaccines, for expressing antigenic proteins and proteins that elevate immunological functions. Further, they may be also useful as in vitro gene transfer vectors for analyzing gene functions. Further, the vectors can be also used to produce proteins of interest. They are also useful as vectors for production of a library that expresses nonspecific cDNA molecule species, such as a cDNA expression library.

BEST MODE FOR CARRYING OUT THE INVENTION

The present invention will be specifically described by way of examples as follows. However, this invention should not be limited to these examples.

EXAMPLE 1

FACS-GAL Analysis

FACS-GAL analysis (Steven, N. F. et al., Cytometry, 12, 291–301, 1991) was performed in order to utilize the promoter exhibiting the highest activity, by comparing promoter activities in 293 cells and 293T cells. According to the method, each of the promoters to which the lacZ gene was linked downstream were transfected into cells, and the expression distribution of lacZ within those cells was investigated.

293 cells and 293T cells were plated at $2 \times 10^6$ cells per 6-cm tissue culture dish, 16 to 24 hours before transfection. 3 µg of plasmid, having lacZ linked downstream of each of the promoters, and 9 µl of Fugene (Boehringer Mannheim) were mixed into 200 µl fetal bovine serum-free DMEM medium, then were left standing for 5~10 minutes. Thereafter, the plasmids were gently added to the 6-cm dishes plated with either 293 cells or 293T cells. The cells were removed after 24 hours, and then were suspended into 50 µl PBS, followed by incubation at 37° C. for 5 minutes. Then, 50 µl FDG (fluorescein di-b-D-galactopyranoside, Molecular Probe, Eugene, Oreg., catalog No. F1179: 2 mM in 98% distilled water) pre-warmed at 37° C. was added. After incubation at 37° C. for 1 minute, 1 ml PBS was added and the cells were placed on ice for 2 hours. After 2 hours, 20 µl PETG (phenyl ethyl-b-D-thiogalactoside, Sigma, catalog No. P4902) was added to stop the reaction, and the expression distribution of lacZ within the cell was investigated by FACS. As a result, the promoter activity of EF1α was determined to be the highest in 293T cells. Compared to the retroviral promoter, LTR, the promoter activity of EF1α was approximately 100-fold higher, and compared to other promoters, the activity was tens of times higher.

EXAMPLE 2

Amplification of the Selective Marker Gene

To use blasticidin and puromycin as the selective markers, PCR reaction was carried out under the following conditions using the resistant genes of each markers (bs$^r$: Kamakura, T. et al., Agric. Biol. Chem., 51, 3165–3168, 1987; puro$^r$: Buchholz, F. et al., Nucleic Acids Res., 24, 3118–3119, 1996) as the templates.

The reaction mixture consisted 10 ng template DNA, 5 µl 10× KOD buffer, 5 µl 2 mM dNTP, 2.5 µl of each 10 µM primers (the base sequence of the primers are shown below), 2 μl 25 mM MgCl$_2$, and 1 μl 2.5 U/ml KOD DNA polymerase (TOYOBO).

The primers used for the blasticidin resistant gene (bs$^r$) were 5'-AAAACATTTAACATTTCTCAACAAG-3' (SEQ ID NO: 1) and 5'-ACGCGTCGACTTAATTTCGGG-TATATTTGAGTG-3' (SEQ ID NO: 2), and those for the puromycin resistant gene (puro$^r$) were 5'-ACCGAGTA-CAAGCCCACG-3' (SEQ ID NO: 3) and 5'-ACGCA-GATCTTCAGGCACCGGGCTTG-3' (SEQ ID NO: 4). The temperature conditions were 94° C. for 30 seconds, 25 cycles of 94° C. for 30 seconds•54° C. for 30 seconds•72° C. for 2 minutes, and 72° C. for 10 minutes. After restriction enzyme treatment of the blasticidin resistant gene (bs$^r$) with SalI and the puromycin resistant gene (puro$^r$) with BglII, electrophoresis followed by extraction from the gel was performed. QiaexII (QIAGEN) was used for the extraction.

EXAMPLE 3

Preparation of pMX-IRES-EGFP

The IRES (internal ribosomal entry site) sequence is a sequence existing in the 5'-noncoding region of the viral mRNA, and is thought to form a characteristic secondary structure. Protein translation of the host is inhibited due to the recognition of this sequence by the ribosome that initiates translation, which allows a predominant translation of the viral protein. To link the selective marker resistant gene behind the IRES, pMX-IRES-EGFP (Nosaka, T. et al., EMBO J., 18, 4754–4765, 1999) was digested with NcoI. After ethanol precipitation, blunt ends were made via Klenow reaction. After phenol/chloroform treatment and ethanol precipitation thereafter, restriction enzyme treatment with SalI to insert bs$^r$, or treatment with BglII to insert puro$^r$ was carried out followed by ligations of each construct. Thus, the selective marker resistant gene was positioned behind the IRES. IRES-bs$^r$ fragment was cut out from pMX-IRES-bs$^r$ by digesting with NotI (TAKARA) and SalI, while IRES-puro$^r$ fragment was cut out from pMX-IRES-puro$^r$ with NotI and BglII.

EXAMPLE 4

Amplification of gag-pol and Ecotropic env

PCR for gag-pol and ecotropic env were performed under the following conditions.

The reaction mixture consisted 10 ng template DNA (Shinnick, et al., Nature, 293, 543, 1981), 5 μl 1× LA Taq buffer, 8 μl 2 mM dNTP, 1 μl of each 10 μM primers (the nucleotide sequences are shown below), and 0.5 μl 5 U/ml LA Taq (TAKARA).

The primers used for amplification of gag-pol were 5'-CGAATTCGCCGCCACCATGGGCCAGACT-GTTACCACTCCCTTAA-3'(SEQ ID NO: 5) and 5'-TACGCCGGCGCTCTGAGCATCAGAAGAA-3' (SEQ ID NO: 6), and those used for amplification of ecotropic env were 5'-CGAATTCGCCGCCACCATGGCGCGT-TCAACGCTCTCAAAA-3' (SEQ ID NO: 7) and 5'-TACGCCGGCGCTATGGCTCGTACTCTAT-3' (SEQ ID NO: 8).

The temperature conditions for gag-pol were 98° C. for 2 minutes, 20 cycles of 98° C. for 20 seconds•68° C. for 3 minutes, and 68° C. for 8 minutes. Those for ecotropic env were 98° C. for 2 minutes, 30 cycles of 98° C. for 20 seconds•68° C. for 2 minutes, and 68° C. for 7 minutes.

After electrophoresis of the PCR products, DNAs were extracted from the gel with QiaexII (QIAGEN). These DNAs were subcloned into TA vectors using the Original TA cloning kit (Invitrogen), and were digested with EcoRI and NotI (TAKARA).

EXAMPLE 5

Construction of gag-pol Expression Vector and Ecotropic env Expression Vector

To express either gag-pol-IRES-bs$^r$ or env-IRES-puro$^r$ under the control of EF1α, the respective sequences were inserted into pCHO (Hirata, Y. et al., FEBS Letter, 356, 244–248 (1994); Okayama, Y. et al., Biochem. Biophys. Res. Commun., 838–45 (1996); pCHO is derived from pEF-BOS (Mizushima, S. and Nagata, S., Nucleic Acids Res., 18, 5332, (1990)) as described below.

[pCHO (gag-pol-IR S-bs$^r$)]

After restriction enzyme treatment of pCHO with BamHI (TAKARA), blunt ends were produced via Klenow reaction. Following ligation to the SalI linker d(CGGTCGACCG) (Stratagene) (SEQ ID NO: 9), it was digested with EcoRI and SalI (TAKARA). The gag-pol and IRES-bs$^r$ fragments produced in Examples 2 and 3 were inserted to produce pCHO (gag-pol-IRES-bs$^r$).

[pCHO(ecoenv-IRES-puro)]

After restriction enzyme treatment of pCHO with EcoRI and BamHI (TAKARA), ecotropic env and IRES-puro$^r$ produced in Examples 2 and 3 were inserted to produce pCHO (ecoenv-IRES-puro).

EXAMPLE 6

Construction of Amphotropic env Expression Vector

While ecotropic env can infect only those cells derived from the same species, amphotropic env can infect a variety of cells. Using this amphotropic env, the env-IRES-puro$^r$ expression vector was constructed as in Examples 4 and 5. The reaction mixture was contained 10 ng plasmid in which the amphotropic env gene (4070A) (Ott, D. et al., J. Virol. 64. 757–766, 1990) was inserted, 5 μl 10× KOD buffer, 5 μl 2 mM dNTP, 2.5 μl of each 10 μM primers (the nucleotide sequences are shown below), 2 μl 25 mM MgCl$_2$, and 1 μl 2.5 U/ml KOD DNA polymerase (TOYOBO). 5'-CGAAT-TCGCCGCCACCATGGCGCGT-TCAACGCTCTCAAAA-3' (SEQ ID NO: 10) and 5'-AT-GCGGCCGCTCATGGCTCGTACTCTAT-3' (SEQ ID NO: 11) were used as primers. The temperature conditions were 98° C. for 3 minutes, 25 cycles of 98° C. for 15 seconds•65° C. for 2 seconds•72° C. for 30 seconds, and 72° C. for 10 minutes.

pCHO (ecoenv-IRES-puro) produced in Example 5 was digested with EcoRI and NotI, and blunted via Klenow treatment. The amphotropic env above was then ligated to produce pCHO (amphoenv-IRES-puro).

EXAMPLE 7

Establishment of Packaging Cells

The 293T cells derived from human mesonephric cells, (DuBridge, R. B. et al., Mol. Cell. Biol., 7, 379–387. 1987) were transfected with the prepared construct. The 293T cells were plated at $2\times10^6$ cells per 6-cm tissue culture dish, 16~24 hours before transfection. 3 µg pCHO (gag-pol-IRES-bs') and 9 µl Fugene (Boehringer Mannheim) were mixed with 200 µl fetal bovine serum-free DMEM media, and the mixture was left standing for 5 to 10 minutes. Then, the mixture was gently added to the 6-cm dish plated with 293T cells. Cells were removed 48 hours later, plated onto a 10-cm dish, and were added to them DMEM media containing 10% fetal bovine serum (8 µg/ml blasticidin).

Approximately 10 days later, each of pCHO (ecoenv-IRES-puro) and pCHO (amphoenv-IRES-puro) were transfected similarly, and then were cultured in a medium containing both of puromycin (0.8 µg/ml) and blasticidin (8 µg/ml). The packaging cells of interest were established by obtaining single clones by limiting dilution at the time when proliferation of the cells had occurred.

The packaging cell in which the ecoenv expression vector was introduced was named "Platinum-E cell (PLAT-E cell)". The cell was deposited as "Pt-E" to a depositary institution as described below.

(a) Name and address of the depositary institution
   Name: National Institute of Bioscience and Human-Technology, Agency of Industrial Science and Technology
   Address: 1-1-3 Higashi, Tsukuba-shi, Ibaraki, Japan (Postal code number: 305-8566)
(b) Date of deposition (Date of original deposition): May 31, 1999
(c) Accession number: FERM BP-6737

Moreover, the packaging cell in which the amphoenv expression vector was introduced was named "Platinum-A cell (PLAT-A cell)". The cell was deposited as "Plat-A" to a depositary institution as described below.

(a) Name and address of the depositary institution
   Name: National Institute of Bioscience and Human-Technology, Agency of Industrial Science and Technology
   Address: 1-1-3 Higashi, Tsukuba-shi, Ibaraki, Japan (Postal code number: 305-8566)
(b) Date of deposition (Date of original deposition): Dec. 22, 1999
(c) Accession number: FERM BP-6977

EXAMPLE 8

Production of Retroviruses

To investigate the infection efficiency of the viral solution obtained from the packaging cells, an infection experiment was performed by the following method. Packaging cells (ecoenv-introduced PLAT-E cells) were plated at $2\times10^6$ cells per 6-cm tissue culture dish, 16 to 24 hours before transfection. 3 µg vector DNA (pMX-GFP: Onishi, M. et al., Exp. Hematol., 24, 324–329, 1996), which is a retroviral vector carrying MoLuLV as its basic framework and to which GFP is inserted, and 9 µl Fugene were mixed with 200 µl serum-free DMEM media, and was left standing for 5 to 10 minutes. This was then added gently to the 6-cm dish plated with the packaging cells.

The supernatant (virus solution) was collected 48 hours later and was centrifuged at 3,000 rpm for 5 minutes. To 500 µl of this solution, 5 µl of 1 mg/ml Polybrene (Sigma) and 1 µl of ×1000 IL3(R and D) were added, and was infected to $1\times10^5$ BaF/3 cells for 5 hours. After 5 hours, 500 µl RPMI1640 media (containing IL3) were added. 24 hours later, taking advantage of the property of GFP expressed in the infected cells, that is, the property that it is excited by light at a wavelength of 395 nm and cause emission of light at a wavelength of 509 nm, infection efficiency was measured as the proportion of cells emitting light (i.e. infectively expressing) using FACScan (fluorescein activated cell sorter: Becton-Dickinson). The infection efficiency towards BaF/3 cells reached 95%, even without concentration of the virus solution.

Measurement of infection efficiencies of the virus solutions obtained from PLAT-E (ecoenv-introduced PLAT-E cells) and BOSC23, thawed simultaneously from liquid nitrogen, using BaF/3 cells revealed that the infection efficiencies after 7 days from the beginning of the passage was 90% or more for both packaging cells. On the other hand, after 2 months of passage, whereas the infection efficiency decreased to 23% when the BOSC23 (Pear et al., Proc. Natl. Acad. Sci. USA, 90:8392–8396, 1993) was used, infection efficiency as high as that after 7 days was confirmed to be maintained even after 2 months of passage, as well as after 4 months of passage (after 4 months from the beginning of the passage, infection efficiency of 70% or more was maintained towards BaF/3 cells) when PLAT-E was used. That is, for approximately 4 months it was possible to produce retroviruses at titers of approximately $1\times10^7$/ml.

When the infection efficiency of virus solution obtained from PLAT-A cells was measured using BaF/3 cells, a value of 30% was confirmed on the 7th day from passage initiation (titer of approximately $1\times10^6$/ml).

EXAMPLE 9

Examination on the Safety of PLAT-E

It was examined whether retroviruses, which have acquired the ability to replicate due to recombination (RCR; replication competent retroviruses), appeared or not while the retrovirus vectors were introduced to the cells.

16 hours after $5\times10^4$ NIH3T3 cells were plated onto 6-cm tissue culture plates, the cells were infected with viruses using 1 ml of virus solution, to which 10 µl of 1 mg/ml Polybrene was added, produced by introducing pMX-neo into packaging cells. 3 ml 10% FCS DMEM was added after 4 hours and cultivation was continued until confluence was reached. Following one passage, the system was cultured until 50% confluence was reached in DMEM supplemented with Polybrene at a final concentration of 2 µg/ml. Then, the medium was exchanged and cultivation was continued for 2 to 3 days in 2 ml of DMEM. The supernatant was passed through a 0.45 µm filter, infected newly to NIH3T3 cells, and selectively cultivated in DMEM containing G418 (neo). If retroviruses having the ability to replicate were produced, a G418 resistant colony should have appeared. However, such colonies were not detected.

EXAMPLE 10

Examination on the Stability of Plat-E Cells Compared to Those of Bosc23 Cells and Phoenix-E Cells The present inventors compared Plat-E cells in its initial progress to Bosc23 cells and Phoenix-E (Nolan Laboratory in the Department of Molecular Pharmacology/the Department of Microbiology and Immunology in the School of Medicine at Stanford University) cells in terms of its ability or inability to produce retroviruses at a high titer with long-term stability by transient transfection. The cultivation conditions for the three packaging cell lines were as follows: According to the manufacturer's instructions, the Bosc23 cells were proliferated in DMEM containing GPT selective reagent (Specialty Media, Lavallette, N.J., USA) supplemented with 10% fetal bovine serum. Phoenix-E cells were classified by FACS using the expression of CD8 as an index, were cultured for one week in DMEM containing hygromycin (300 µg/ml) and diphtheria toxin (1 µg/ml) supplemented with 10% fetal bovine serum, and then were transferred to DMEM supplemented with 10% bovine fetal serum which doesn't contain hygromycin and diphtheria toxin. Plat-E cells were maintained all the time in DMEM containing blasticidin (10 µg/ml) and puromycin (1 µg/ml) supplemented with 10% fetal bovine serum. The infection efficiency of retroviruses produced from Bosc23 diminished within 3 months and that of retroviruses produced from Phoenix-E cells diminished similarly. On the other hand, retroviruses produced from Plat-E retained an average titer of approximately $1 \times 10^7$/ml to NIH3T3 cells for at least 4 months under conditions of drug selective pressure and an infection efficiency of 75% or more (maximum of 99%) to BaF/3 cells when they were transfected transiently.

To compare the expression level of Gag-pol and env mRNA in Plat-E, Bosc23, and Phoenix-E packaging cell lines, Northern blot analysis was performed using cells cultured for 3 weeks. The expression level of Gag-pol and env mRNA in Plat-E cells were 4-fold and 10-fold more, respectively, compared to other cell lines.

RT activity in the cell lysate was also analyzed. The RT activity in Plat-E cells was detected to be at least twice as high as that in Bosc23 and Phoenix-E cells. Furthermore, the expression level of the env protein evaluated by antibody staining using antibodies raised against the env gene product was considerably higher than that in Bosc23 and Phoenix-E cells.

Therefore, it was indicated that Plat-E cells could produce retroviruses at high titer with long-term stability.

INDUSTRIAL APPLICABILITY

A virus-producing cell that sustains the ability to produce infectious viruses at high titer even after long term passages is provided according to the present invention. Additionally, a method for producing infectious viruses at high titers using the virus producing cells is also provided. The use of retroviral packaging cells of this invention enables the stable provision of retroviruses with high titers. In addition, by minimizing the viral genome to be included in the packaging cell, the inventors successfully lowered the possibility of the emergence of undesirable recombinant viruses, such as replication competent retroviruses (RCR). Therefore, the retroviral packaging cells of this invention serve as powerful tools for producing retroviral vectors in fields of biology and medical research, and are useful for producing gene transfer vectors used in gene therapy.

The invention claimed is:

1. A 293T cell useful for the production of retroviruses, wherein the cell contains an expression construct comprising DNA encoding gag, pol, and env retroviral structural proteins operably linked downstream of an EF1α promoter.

2. A 293T cell useful for the production of retroviruses by expressing retroviral structural proteins gag, pol and env, wherein the cell comprises a first expression construct expressing gag and pol from an EF1α promoter, and a second expression construct expressing env from an EF1α promoter.

3. The cell according to claim 1, wherein the env is derived from either an ecotropic retrovirus or an amphotropic retrovirus.

4. A cell specified by Accession No. FERM BP-6737 or FERM BP-6977 as deposited at the National Institute of Bioscience and Human-Technology in Japan.

5. The cell according to claim 1, wherein a Kozak's consensus sequence is located upstream of a translation initiation codon of the DNA encoding the retroviral structural proteins in the expression construct.

6. The cell according to claim 1, wherein the DNA encoding the retroviral structural proteins is linked to a DNA encoding a selective marker via an IRES sequence.

7. The cell according to claim 1, wherein the DNA encoding the retroviral structural proteins is substantially free from virus genome-derived DNA other than the DNA encoding gag, pol, and env.

8. A method for producing a retrovirus, the method comprising the step of introducing into the cell of claim 1 a retroviral vector DNA that lacks sequence encoding gag, pol, and env.

9. The method according to claim 8, in which a foreign coding sequence is included in the retroviral vector DNA.

10. The cell according to claim 2, wherein the env is derived from either an ecotropic retrovirus or an amphotropic retrovirus.

11. The cell according to claim 2, wherein a Kozak's consensus sequence is located upstream of a translation initiation codon of the DNA encoding the retroviral structural proteins in each of the first and second expression constructs.

12. The cell according to claim 2, wherein the DNA encoding the retroviral structural proteins in each of the first and second expression constructs is linked to a DNA encoding a selective marker via an IRES sequence.

13. The cell according to claim 2, wherein the DNA encoding the retroviral structural proteins in the first and second expression constructs is substantially free from virus genome-derived DNA other than the DNA encoding gag, pol, and env.

14. A method for producing a retrovirus, the method comprising the step of introducing into the cell of claim 2 a retroviral vector DNA that lacks sequence encoding gag, pol, and env.

15. The method according to claim 14, in which a foreign coding sequence is included in the retroviral vector DNA.

16. A method for producing a retrovirus, the method comprising the step of introducing into the cell of claim 4 a retroviral vector DNA that lacks sequence encoding gag, pol, and env.

17. The method according to claim 16, in which a foreign coding sequence is included in the retroviral vector DNA.

* * * * *

UNITED STATES PATENT AND TRADEMARK OFFICE
CERTIFICATE OF CORRECTION

PATENT NO.        : 6,995,009 B1
APPLICATION NO.   : 10/009329
DATED             : February 7, 2006
INVENTOR(S)       : Toshio Kitamura and Sumiyo Morita Page 1 of 1

It is certified that error appears in the above-identified patent and that said Letters Patent is hereby corrected as shown below:

Title Page

Item (56) References cited, Other publications, listing number 3, line 2 of right column, delete "*kouguku*" and insert --*kougaku*--

Item (56) References cited, Other publications, listing number 11, line 28 of right column, delete "Safety" *Virology*, vol. 218" and insert --Safety", *Virology*, vol. 218--

Signed and Sealed this

Third Day of July, 2007

JON W. DUDAS
*Director of the United States Patent and Trademark Office*